(12) United States Patent
Janssens et al.

(10) Patent No.: US 7,768,643 B1
(45) Date of Patent: Aug. 3, 2010

(54) APPARATUS AND METHOD FOR CLASSIFYING AND SORTING ARTICLES

(75) Inventors: Carlo Janssens, Londerzeel (BE); Johan Calcoen, Wilsele (BE)

(73) Assignee: Key Technology, Inc., Walla Walla, WA (US)

( * ) Notice: Subject to any disclaimer, the term of this patent is extended or adjusted under 35 U.S.C. 154(b) by 953 days.

(21) Appl. No.: 11/392,947

(22) Filed: Mar. 30, 2006

(51) Int. Cl.
*G01J 4/00* (2006.01)
(52) U.S. Cl. ..................................... 356/369
(58) Field of Classification Search ................. 356/369; 250/559.09, 225
See application file for complete search history.

(56) References Cited

U.S. PATENT DOCUMENTS

| | | | | |
|---|---|---|---|---|
| 3,097,744 | A * | 7/1963 | Leaver et al. | 209/564 |
| 4,630,736 | A * | 12/1986 | Maughan et al. | 209/587 |
| 5,151,822 | A * | 9/1992 | Hekker et al. | 359/559 |
| 5,297,667 | A * | 3/1994 | Hoffman et al. | 198/493 |
| 5,887,073 | A | 3/1999 | Fazzari et al. | |
| 6,003,681 | A * | 12/1999 | Wilbur et al. | 209/639 |
| 6,122,404 | A | 9/2000 | Barter et al. | |

FOREIGN PATENT DOCUMENTS

WO     WO 02/31473 A1     4/2002

OTHER PUBLICATIONS

G. Vogtmeier, et al., "Polarization analysis system for very rough surfaces," Institute for Highfrequency Technology, RWTH Aachen, Germany, SPIE vol. 3121, 0277-786X/97, pp. 74-85.
James K. Boger, et al., "Issues in a broadband 4-channel reduced Stokes polarimeter," Polarization Analysis, Measurement, and Remote Sensing IV, Dennis Goldstein, David Chenault, Walter Egan, Michael Duggin, Editors, Proceedings of SPIE vol. 4481 (2002), 0277-786X/02, pp. 311-321.
Michael Shirbak, "Fiber optic sensor for birefringence," Polarization Analysis, Measurement, and Remote Sensing IV, Dennis Goldstein, David Chenault, Walter Egan, Michael Duggin, Editors, Proceedings of SPIE vol. 4481 (2002), 0277-786X/02, pp. 175-179.
Mircea Mujat, et al., "Polarimetric signature of dense scattering media," Proceedings of SPIE vol. 5158 Polarization Science and Remote Sensing, edited by Joseph A. Shaw, J. Scott Tyo (SPIE, Bellingham, WA, 2003), 0277-786X/03, pp. 217-225.
Ajaina Nezhuvingal, et al., "Mueller Matrix Optical Imaging with Application to Tissue Diagnostics," SPIE USE, V. 3 4961A-24, p. 1-10, Feb. 19, 2003.
Matthew H. Smith, et al., "Muller matrix imaging polarimetry in dermatology," Biomedical Diagnostic, Guidance, and Surgical-Assist Systems II, T. Vo-Dihn, W.S. Grundfest, D.A. Benaron, eds., Proceedings of SPIE vol. 3911, 2000.

* cited by examiner (Continued)

*Primary Examiner*—Roy Punnoose
(74) *Attorney, Agent, or Firm*—Harness, Dickey & Pierce, P.L.C.

(57) ABSTRACT

An apparatus for classifying articles may include a frame connected to (1) transport means for directing articles to create a product stream, (2) an emitter section having a radiation source and (3) a detection section for detecting a portion of radiation reflected by articles. The detection section may include first detection means for converting radiant power of reflected radiation having a first polarization state into a first electrical signal, second detection means for converting radiant power of reflected radiation having a second polarization state into a second electrical signal, and third detection means for converting radiant power of reflected radiation into a third electrical signal. Control circuitry, which may receive the electrical signals, may include decision means for generating a selection signal. Selection means may separate an article from the product stream according to the received selection signal from the control circuitry.

42 Claims, 8 Drawing Sheets

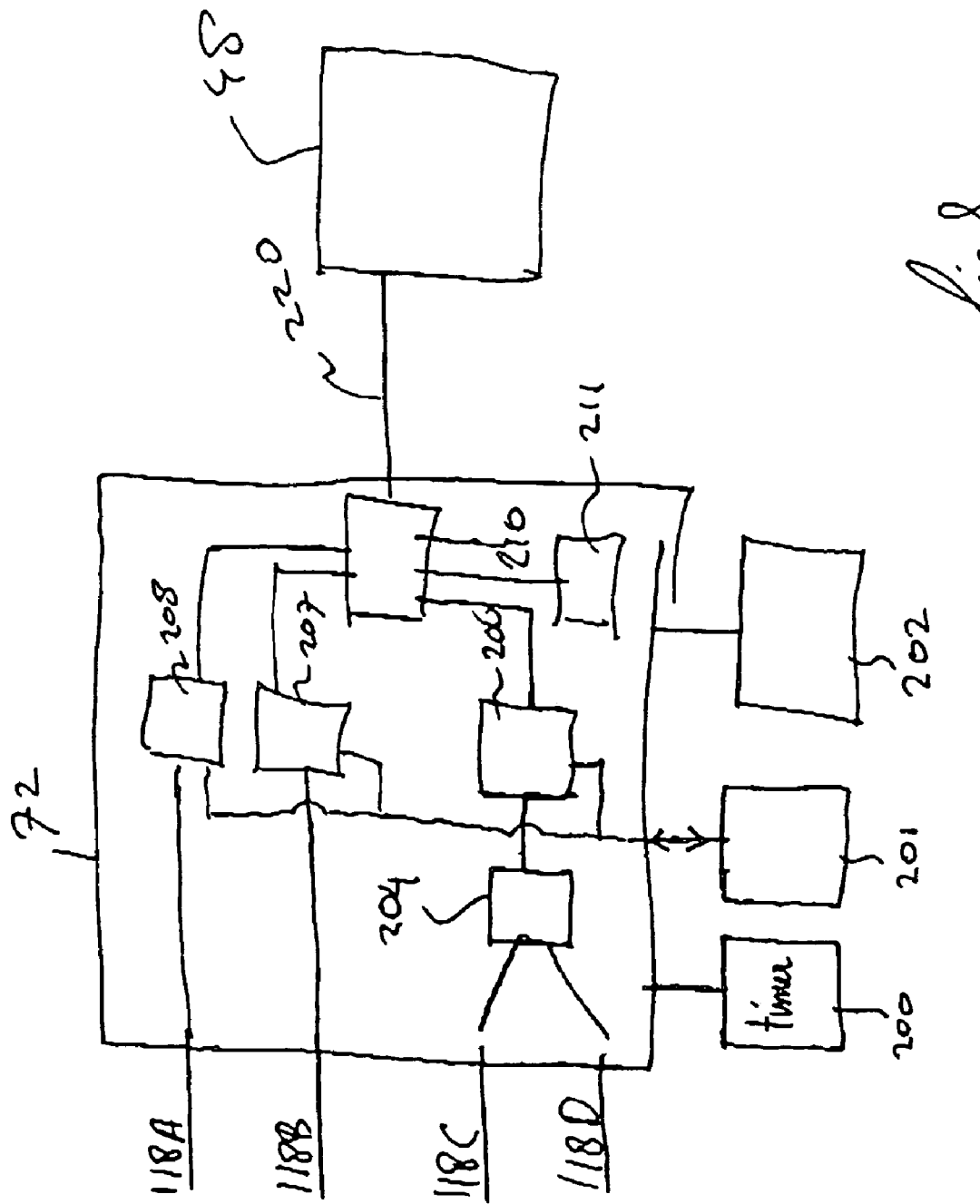

APPARATUS AND METHOD FOR CLASSIFYING AND SORTING ARTICLES

FIELD OF THE INVENTION

The present invention relates generally to an apparatus and method for classifying articles wherein the apparatus includes elements to transmit electromagnetic radiation towards a product stream containing both desirable and undesirable articles and further elements to receive the electromagnetic radiation that has been reflected, which includes specular as well as diffuse scattering, from the articles in the product stream and further includes elements to label each article as a desirable or undesirable article based on the received electromagnetic radiation.

BACKGROUND OF THE INVENTION

Classifying and sorting apparatuses have been known in the art for many years and are useful for separating desirable and undesirable articles from a product stream using a variety of methods. The apparatus often found in the art include reflecting electromagnetic radiation in the form of light to determine the optical reflective characteristics of the articles in the product stream using color as a determinant. A notable example of such as sorter is the High Speed Mass Flow Sorting Apparatus for Optically Inspection and Sorting Bulk Food Products as shown in U.S. Pat. No. 5,887,073, which is incorporated by reference U.S. Pat. No. 6,122,404 teaches a visible stokes polarimetric imager that uses a plurality of prisms and filters in conjunction with a imaging device. This device is disadvantaged because the imaging requires the optics to provide minimal distortion across the entire field of view. This requirement increases both the cost of the components as well as the initial setup and calibration requirements. Each pixel in a sensor array needs to be calibrated. Yet further, the imager requires a significant light input which increases the cost and energy requirements of the imager. The document is incorporated by reference.

The PCT publication WO 02/31473A1, also incorporated by reference, specifically teaches that the reflected light received from the products having the same polarization as the light beam generally does not contain useful information and is allowed to pass through the beam splitter and directed away from the detectors and not considered in the sorting decision process. It is also indicated that reflected radiation having the same polarization as the initial polarization does not contain useful information.

The subject invention for an apparatus and method for classifying and sorting articles overcomes the perceived shortcomings and detriments in the prior art apparatuses and methods and is the subject of the present patent.

OBJECTS AND SUMMARY OF THE INVENTION

It is a primary object of the principal invention to provide an improved sorting machine and method.

It is also an object of the present invention to provide a laser sorting machine and method that can sort various types of products by a combination of different signals relating to structure.

Additional objects and advantages of the invention will be set forth in part in the following description, or may be obvious from the description, or may be learned through practice of the invention.

According to an aspect of the invention an apparatus for classifying articles is provided. The apparatus comprises transport means connected to a frame for directing articles having a transport direction, such that a product stream is created. At least an emitter section is provided, connected to the frame, wherein the emitter section comprises at least one radiation source of electromagnetic radiation having at least a first wavelength and an initial polarization ($P_0$) The radiation, preferably a light beam, such as an intense beam from a laser, is directed towards a scanning zone. The articles are moved through the scanning zone. At least a detection section is connected to the frame for detecting at least a portion of radiation reflected by articles in the scanning zone. The detection section has at least a first detection means for converting a first polarization state ($P_1$) of the reflected radiation into a first electrical signal ($E_1$), at least a second detection means for converting a second different polarization state ($P_2$) of the reflected radiation into a second electrical signal ($E_2$), and a third detection means for converting the radiant power of the reflected radiation into a third electrical signal (I). Further control circuitry is in operable communication with the detection section for receiving the electrical signals, wherein the control circuitry comprises decision means for generating a selection signal ($S_1$) based on the received electrical signals and threshold values from a memory. Selection means for separating products from the product stream are arranged downstream from the detection section, wherein the selection means are actuated to separate an article from the product stream according to the received selection signal ($S_1$) from the control circuitry. The apparatus has an improved contrast since two polarization signals are measured and converted in electrical signal. The two polarization signals generate a large contrast for dark articles. Contrary to the teaching of WO 02/31473 A1 at least a part of the information corresponding to the initial state of polarization is measured, converted and used in the decision algorithm for classification. A combination of two different polarization states always includes at least a component of the initial polarization state.

Preferably the polarization signals correspond to are mutual orthogonal polarizations. Preferably one of the polarization signals corresponds with the initial state of polarization.

According to a further aspect of the invention a method is provided for classifying products. A product stream is provided. The products are scanned by emitting toward the product stream electromagnetic radiation having an initial polarization. At least two electrical signals corresponding to different polarization states of the reflected radiation from the scanned product are generated. A third electrical signal corresponding to the radiant power of the reflected light is also generated. Classification of the article in the product stream based on the generated electrical signals and selection values inputted by the user and redirecting the product from the stream based on the decision results.

Preferred embodiments are disclosed in the subclaims.

BRIEF DESCRIPTION OF THE DRAWINGS

Preferred embodiments of the invention are described below with reference to the following accompanying drawings.

FIG. 8 shows a schematic illustration of the decision making process.

DETAILED DESCRIPTION

Figure 1:
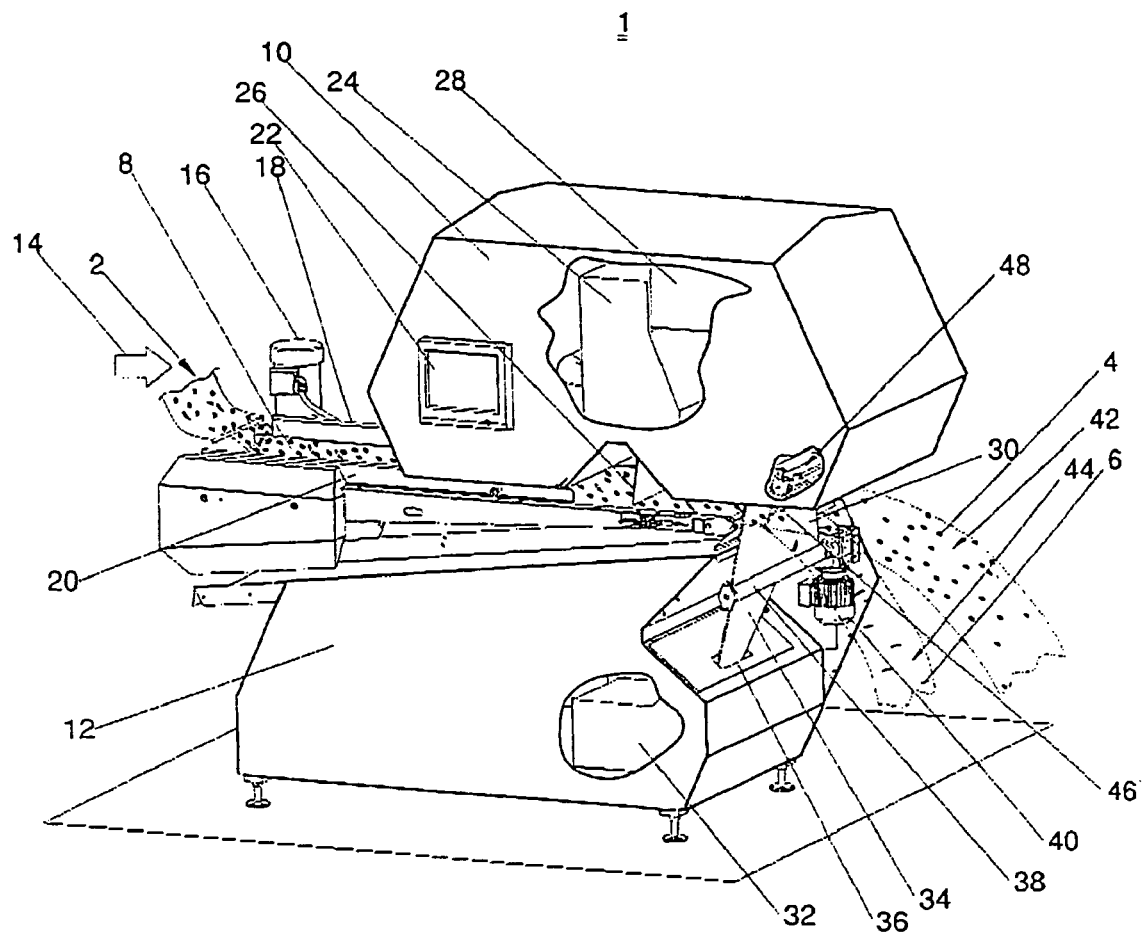
FIG. 1 is a perspective view of the classifying and sorting apparatus.

In accordance with the invention, an apparatus is provided for sorting products moving through a detection zone wherein it is desired to detect and remove irregularities or foreign objects from the product stream. The product stream is created using a transport means whereupon articles are deposited. The transport means convey the articles through a scanning zone.

The invention is not limited to use for any particular type of product, and is particularly useful for scanning food products, such as raisins, vegetables, nuts, shellfish, etc. The invention is useful in any application wherein irregular products or foreign objects in the product stream can be detected by structure characteristics such as surface characteristics, body characteristics such as translucency and/or color differences.

Electromagnetic radiation used for scanning the products is provided in the apparatus in the emitter section. The reflected radiation is detected in the detection section.

The emitter section includes a radiation source, preferably at least one laser. The radiation source can direct a concentrated light beam having a relatively small cross-sectional area towards a scanning zone. The products move through the scanning zone and are impinged upon by the light beam. The products can be conveyed or propelled through the scanning zone by various devices.

The radiation source can emit electromagnetic radiation having a first polarized state. The source could be a laser. The emitter section can include a filter means in particular a polarization filter, in particular a polarization filter corresponding to the polarization state of the source. Polarizing a laser is easier and more efficient then lamps, and most commercially available diode lasers and solid state lasers are already linearly polarized. Use of an extra polarization filter on top of an already linearly polarized laser could increase the purity of polarization.

In an embodiment, the products are propelled through the scanning zone in a "free-flight" configuration wherein a conveyor moving at a relatively high speed propels the objects across the scanning zone.

The light reflected from the products includes light directly (surface) reflected from the point of impingement of the light beam on the products and light that is reflected by body scattering or body back scattering from the area surrounding the impingement point due to diffusion or scattering of the light beam into the product. Surface reflection includes direct reflection, as if the surface is a mirror, and diffuse reflection, wherein radiation is reflected a couple of times on the surface. Body back scattering refers to radiation penetrating the body of the product, scattering of the radiation inside the body, where after the radiation returns.

The degree of diffusion of the light into the product depends on the translucency of the product. For example, if the scanned body is a relatively non-translucent body (such as certain stones), relatively little light will be diffused into the product and substantially all of the reflected light is directly reflected from the point of impingement of the light beam on the product. On the other hand, if the scanned product is a relatively translucent body (such as certain food products), a large portion of the impinging radiation will diffuse into the translucent body and will be reflected as diffused or scattered light from the area surrounding the impingement point.

In one embodiment a detection section is disposed to receive the light reflected back from the scanned products. The detection section according to the invention comprises several detection means. The detection means converts an radiant power of received radiation into a corresponding electrical signal. The electrical signal can be interpreted. The electrical signal could be a digital signal. Preferably at least one of the detector means 110, 112, 114 and/or 116 is detector using a single, flying spot approach, wherein the disadvantage of calibration for each pixel of the sensor array is avoided.

At least one of the detection means 110, 112, 114, 116 could have an instantaneous field of view larger than the cross-sectional area of the light beam so as to be sensitive to substantially all of the direct and diffused reflected light from the products. This detector can generates an electrical signal corresponding to the received total (direct and diffused) reflected light.

In an embodiment at least one of the detection means 110, 112 is disposed to receive the reflected light back from the products having a different ("second") field of view generally of the same order of magnitude as the cross-sectional area of the light beam. The field of view could be equal to the cross-sectional area of the beam. However, because the light gets diffusely reflected even on the surface, a field of view about 2-3 times larger then the beam is preferred, especially in combination with the scanning and classifying of bright surfaces. In this way, this detection means is sensitive to substantially only the surface reflected light from the products. The detection means can generate a corresponding electrical signal. A diaphragm can be placed in the trajectory of reflected light 122, 123 just before it reaches the detector 110, 112.

In an embodiment at least one of the detection means 110, 112 is disposed to receive the reflected light back from the products the detection means having a field of view generally relating to the reflected light which is a result of body backscattering. This is body back-scattered light outside the cross-sectional area of the impingement light beam. In this way, this detection means is sensitive to substantially the scattered reflected light from the products. The detection means can generate a corresponding electrical signal.

According to an embodiment the detection means comprises a diaphragm. For detecting back scattered reflection a 'Mercedes' (trademark) sign shaped diaphragm is state of the art. The Mercedes sign comprises a star with a center, wherein the center is adapted to block radiation from surface reflection. The diaphragm is placed in the trajectory 120, 122, 123 of the reflected light before reaching a detector.

A detection means has a linear scale. The linear scale allows to measure a contrast. The measurement is converted into an electrical signal, preferably a digital signal. An aspect of the invention relates to improving certain ranges of the detected radiant power or reflectance. In a preferred embodiment the invention improves the contrast for dark articles.

One of more beam splitters 102, 108, 106 may be utilized in the detection section upstream of the detection devices. The beam splitter is disposed to split the reflected light from the products into a first beam directed to a first detector and a second beam directed to a second detector.

It may also be desired to utilize a device for "filtering" a portion of the reflected radiation before feeding the reflection to the detection means. The filter can be placed in the trajectory 78, 119, 120 of the reflected light.

For example, a polarizing beam splitter 108 may be disposed between the scanning zone and the detection devices. The polarizing beam splitter is adapted to allow the reflected radiation received from the products with respect to a first direction of polarization and directs or deflects reflected radiation in a second, different direction of polarization. The radiation having first and second polarization is preferably directed to different detection means Preferably the first direction of polarization is parallel to the initial state of polarization of the radiation emitted in the emitter section.

The polarizing beam splitter 108 is preferably is wire grid polarizer 150. The polarizing beam splitter 150 comprises a glass substrate 151 whereupon metal wires 152, microwires, are deposited. Preferably aluminum microwires are used.

The first and second detector configuration may be utilized with a laser to sort by structure alone. It should be appreciated that any combination of laser, mirrors, focusing lenses, and beam splitters may be configured to analyze the reflected light beam by a number of different detector types to sort by structure.

The apparatus also preferably includes a selection means, e.g. an ejector assembly 48 having nozzles 46, for removal of undesired articles from the product stream such as a bank of air ejectors disposed generally across and downstream from the scanning zone, controlled by the control circuitry and acting in response to the control signals to remove unwanted objects or irregularities from the scanned products. For example, in the embodiment wherein the removal mechanism comprises a bank of air ejectors 46, the air ejectors are of a number and location so as to be able to remove an object from the products from anywhere across the width of the light beam scanning zone.

The scanning or interrogation zone 30 may be defined by a rotating multi-faceted mirror 52 disposed between the light source and the scanning zone. The mirror directs the light beam in a high speed scanning pattern that defines the width of the scanning zone.

According to the invention the Zenith approach is used in the apparatus and method for classifying according to the invention. The scanning mirror is configured to reflect a portion of the electromagnetic emission that is reflected from the articles in the product stream as the electromagnetic signal that is transmitted to the detection section.

According to an aspect of the invention the apparatus comprises a first detection means 114 for converting the radiant power of the reflected radiation having a first polarized state of the reflected radiation. The detection means converts a measured radiant power or flux of the reflected radiation for this first polarized state into an electrical signal, possibly a digital or analog signal. Radiant power is expressed in Watts (W). The electrical output signal 118c of the detection means could be a representation for the radiant power in Watts.

The apparatus further comprises a second detection means 116 for detecting a second, different state of polarization. The second detection means converts a radiant power of the reflected radiation having a second state into an electrical signal 118d.

The combination of the two electrical signals corresponding to the radiant power of two different polarization states is particularly useful as an improvement for contrast and classification of objects having a low reflectance, such as objects reflecting less than 25%, preferably less than 20% of the maximum reflected radiant power. The maximum reflected radiant power can be measured using a test object.

The combination of the two electrical signals 113c and 118d is obtained in the classifier or decision means 72. A programmed computational means 204 combines the two signals e.g according to a formula used for Polarization or Depolarization, see e.g. equation (2) hereunder.

Preferably the measured polarization states are perpendicular. The polarized beam splitter can be a part of the respective detection means.

Preferably a third detection means 110, 112 is installed to detect, simultaneously, the radiant power or flux of non-polarized radiation, preferably scattered radiation.

The first, second and third detection means generate respective electrical signals 118 corresponding to detected values for the reflected radiation according to the different properties.

The combination of respective electrical signals comprises the detected values for a pixel in the scanned zone. A pixel can be formed in the decision means 210 in the classifier. The collecting of the respective combinations of electrical signals during a certain time interval corresponds to building a 2-dimensional image of the scanned zone. For this reason the decision means 210 is connected to a temporary memory 211 for recording and collecting combinations of received signals over a certain period. The interval can be predetermined. A timer 200 can provide the classifier 72 and the decision means 210 with the predetermined interval.

This allows the decision means 210 to base a decision not only on values from a certain pixel but on a combination of pixels comprising the article to be classified. In particular polarization has been proven to be successful in improving the decision means in recognizing edges of scanned products. This improves decisions relating to the size of the scanned products. The decision can be outputted as an electrical signal 220 by the decision means 210 and the classifier 72 to the selection means.

Control circuitry 72 is provided in operable communication with the detector means to receive the electrical signals. The control circuitry, comprising a classifier, generates control or selection signals based on either of the signals individually or on a difference of the signals to sort the scanned products by any combination of color or surface characteristics depending on the exact signal or combination of signals used. In a memory 201, threshold values are saved. The control circuitry 72 is adapted to compare received signals or combination of received signals with these values. The classifier 72 comprises compare means 206, 207, 208 for comparing the input signals 118 and/or combinations thereof with the threshold values from the memory 201. The outcome of the comparison can generate an output signal representing a decision with respect to the scanned article, said output being fed to the selection means. Preferably the decision is based on a combination of outcomes of the respective electrical signals, preferably collected over a period of time.

The control circuitry 72 can comprise an interface 202 for interface with a user. The interface can comprise input means, such as a keyboard and output means such as a display, but also a network connection for outputting calculated data for collecting the information at a remote location.

In a preferred embodiment at least the first and second signals are combined 204 in the control circuitry. Contrary to WO 02/31473 the reflected radiation having generally the same polarization as the radiation emitted by the radiation source is used usefully if the detected values of the first and second polarization are combined. Possible combination of the first and second electrical signals $E_1$ and $E_2$ are:

$$P = E_1 - E_2/(E_2+E_1) \quad (1)$$

or $$D = 1-P = 2E_2/(E_2+E_1) \quad (2)$$

wherein both formulas are known from literature for polarization. The first combination is known as the first normalized Stokes parameter, the second combination can be seen as a degree of depolarization.

The combined first and second electrical signals have proven to be particularly advantageous in situations of low radiation reflection, in particular for objects having low reflectance. A combination 204 of first and second electrical signals is beneficial for creating and increasing contrast and for eliminating glare or haze in certain applications. It is an aspect of the invention to combine the first and second electrical signals.

In particular the contrast for classification was improved according to the invention if the decision means 210 based decisions on a combination of the first and second electrical signals 118c, 118d and a third signal 118a, 118b based on reflected scattered radiation. The contrast increased particularly for diffuse articles in particular dark diffuse articles. A further improved contrast was obtained for dark articles having rough surface structures.

An embodiment according to the invention uses the zenith-approach. The laser viewing angle of the articles is generally 0°. This is achieved using a mirror with a hole forming the interface between the laser side and the detector side. The apparatus is an imaging system.

A polygon mirror is used for scanning. The same polygon mirror can part of the detection and emitter section. It reflects radiation from the emitter section onto the product stream and reflects the reflected radiation into the detections section.

As physical elements such as mirrors, beam splitter surface etc. are used in the apparatus according to the invention, these elements produce circular polarization components. This is due to different reflection and/or transmission of the parallel ('p') and sagittal ('s') polarized radiation. The first and second detection means do not detect the exact reflected polarized radiation from the articles due to intermediate optical components. The detected signals are a linear mix of the reflection from the articles.

It can be assumed that:

$$\begin{pmatrix} C_{1r} \\ C_{2r} \end{pmatrix} = \begin{pmatrix} a_{11} a_{12} \\ a_{21} a_{22} \end{pmatrix} \begin{pmatrix} C_1 \\ C_2 \end{pmatrix} \text{ or } \overline{C}_r = A \cdot \overline{C}$$

wherein $C_{1r}$ and $C_{2r}$ are the (true) reflected signals and $C_1$ and $C_2$ are the measured signals.

The correction of the measured value can be performed in the classifier 72. The correction can be calculated in the decision means 210. The correction values can be saved in a memory 201 connected to the classifier 72.

According to an embodiment the non-diagonal elements can be assumed to be equal to zero.

$A_{11}$ and $a_{22}$ can be obtained in an initialization phase of the apparatus. During initialization a user can obtain and record in a memory 201 of the apparatus values. For initialization preferably a white reference bar, such as a drum, can be used. A HMPE translucent cylinder can be used. Because it is translucent, the drum will show a considerable amount of volume scattering. HMPE is white and will show surface scattering. Contrast is not influenced if it is assumed that such a drum completely depolarizes the incident beam of radiation. Initialization can be started by a user using the interface 202.

The electrical signals received from the detection means can be collected in the control circuitry, in particular in the classifier over a predetermined period. This allows to collect a 'picture' of the scanned products.

These and other aspects of the present invention will be discussed in greater detail hereinafter.

Referring now to FIG. 1, an apparatus for classifying and sorting articles is shown and is generally identified by the numeral 1. The apparatus is shown in receiving relation to a stream of articles designated as the product stream 2. In practice, for example, the product stream 2, may include comestible items such as vegetables or snack food items or may include non-edible items such as wood chips or tobacco leaves. Yet further the product stream may include other non-organic articles such as minerals or gems.

The product stream 2 is composed of individual articles traveling in a direction generally depicted by the arrow 14. The product stream may include individual articles that are moving in concert at a generally uniform speed and traveling in the product flow direction 14. The individual articles often vary parametrically in dimension, density, color, etc. Often, the quality of an article in a product stream may be ascertained and may be divided into desirable articles 4 and undesirable articles 6.

Articles in the product stream 2 are transferred to the feed conveyor 8 for transport through the apparatus for classifying and sorting articles 10. The feed conveyor 8 is driven by conveyor motor 16 in the direction generally indicated by the product flow direction arrow 14. The product stream 2 that is transported on the feed conveyor 8 is bounded by a left product guide 18 which is located on the left side of the feed conveyor 8 when looking in the direction of the product flow 14 and the right product stream guide 20 which is located on the right side of the feed conveyor 8 when looking in the direction of the product flow 14.

The apparatus for classifying and sorting articles 1, has an upper housing 10 and a lower housing 12 which enclose modules that provide the function of classifying and sorting of the articles which will be discussed in further detail below. A user interface 22 is supported and located on the surface of the upper housing 10 and provides a means to receive and deliver information to an operator (not shown). The user interface 22 may utilize a CRT or LCD panel for output and include a keyboard, touchscreen or other input means known in the art. From the user interface 22, the user may view articles in the product stream 2 that have traveled on the belt conveyor 8. Yet further, the user interface 22 provides a means for a user to enter user information to configure the apparatus for classifying and sorting articles 1 for making the determination between a desirable article 4 and an undesirable article 6. The information provided by the user interface 22 may also be provide by a local area network connection (not shown)

Continuing to refer to FIG. 1, an inspection station 24 is located within the upper housing 10 and positioned over the transport means, here formed by a belt conveyor 8 and configured to illuminate and create images of the articles in the product stream 2 as they are transported by the infeed conveyor 8. The inspection station 24 has an inspection zone 26 that is located near the surface of the feed conveyor 8 which defines the area that the articles in the product stream 2 are imaged. An upper interrogation station 28 comprising both the emitter and detection section according to the invention, is located adjacent and downstream from the inspection station 24 being also located in the upper housing 10. The interrogation station 28 has an upper interrogation zone 30 shown underneath the upper interrogation Station 28 and is shown as articles from the product stream 2 penetrate the zone as they are launched from the feed conveyor.

A lower interrogation Station 32 is shown in the lower housing 12 and is directed in an upward direction towards the upper housing 10 and further directed towards the upper interrogation station 28. Each interrogation station includes elements for transmitting electromagnetic energy to the product stream 2 and for receiving and converting electromagnetic energy from the products stream. This electromagnetic energy is propagated through an aperture 36 in the lower housing 12 and another aperture (not shown) in the upper housing 10.

Articles in the product stream 2 are transported on the feed conveyor 8 and launched off of the end of the feed conveyor 8 through the upper interrogation zone 28 and travel in a trajectory that may be characterized as the pass stream 42 for articles that are determined to be desirable articles 4 and the reject stream 44 for articles of the product stream 2 that are determined to be undesirable articles 6. Reflected electromagnetic energy from the articles as a pass through the upper interrogation zone 30 is returned back to the upper interrogation Station 28 indicating the presence of the article so that its characteristics may be further determined by the upper interrogation station 28. When no articles are present in the product stream 2, the electromagnetic energy from the upper interrogation station is reflected from the background 38 which is oriented to reflect the electromagnetic from the upper interrogation station 28 in such a manner as to indicate that there are no articles present. The background 38 can formed by a HMPE translucent cylinder.

In a preferred embodiment of, the interrogation background 38 is rotated about its longitudinal axis by a background rotation motor 40. It has been found that rotating the background is desirable in many applications because it allows for a efficient cleaning of the background using a clean place system (not shown) and is especially important when the background is located at a lower point in the launch point relative to the feed conveyor 8. The lower interrogation station 32 has a companion stationary background (not shown) and is provided in non-rotating form since the stationary background is higher than the launch point from the feed conveyor 8.

As articles in the products stream 2 are transported and launched from the feed conveyor 8 they travel below a plurality of selection means formed in this embodiment by ejector nozzles 46 that are positioned to emit pulses of fluid directed toward the product stream 2 to dislodge certain articles in a product string as they pass underneath. These ejector nozzles 46 are part of the ejector assembly 48 which is commanded by the classification processor (not shown) which receives data from the inspection station 24, the upper interrogation station 28 and the lower interrogation station 32 and compares this data with information entered by the user by means of the user interface 22 to classify the articles in the product stream 2 as desirable articles 4 or undesirable articles 6. For those articles in the product stream 2 that are identified as desirable articles 4 the product stream continues as a pass stream 42. For articles that are identified as undesirable articles 6, a pulse of fluid is emitted by the ejector nozzles as the article travels under the ejector assembly 48 to travel in another trajectory generally indicated by the numeral 44.

Figure 2:
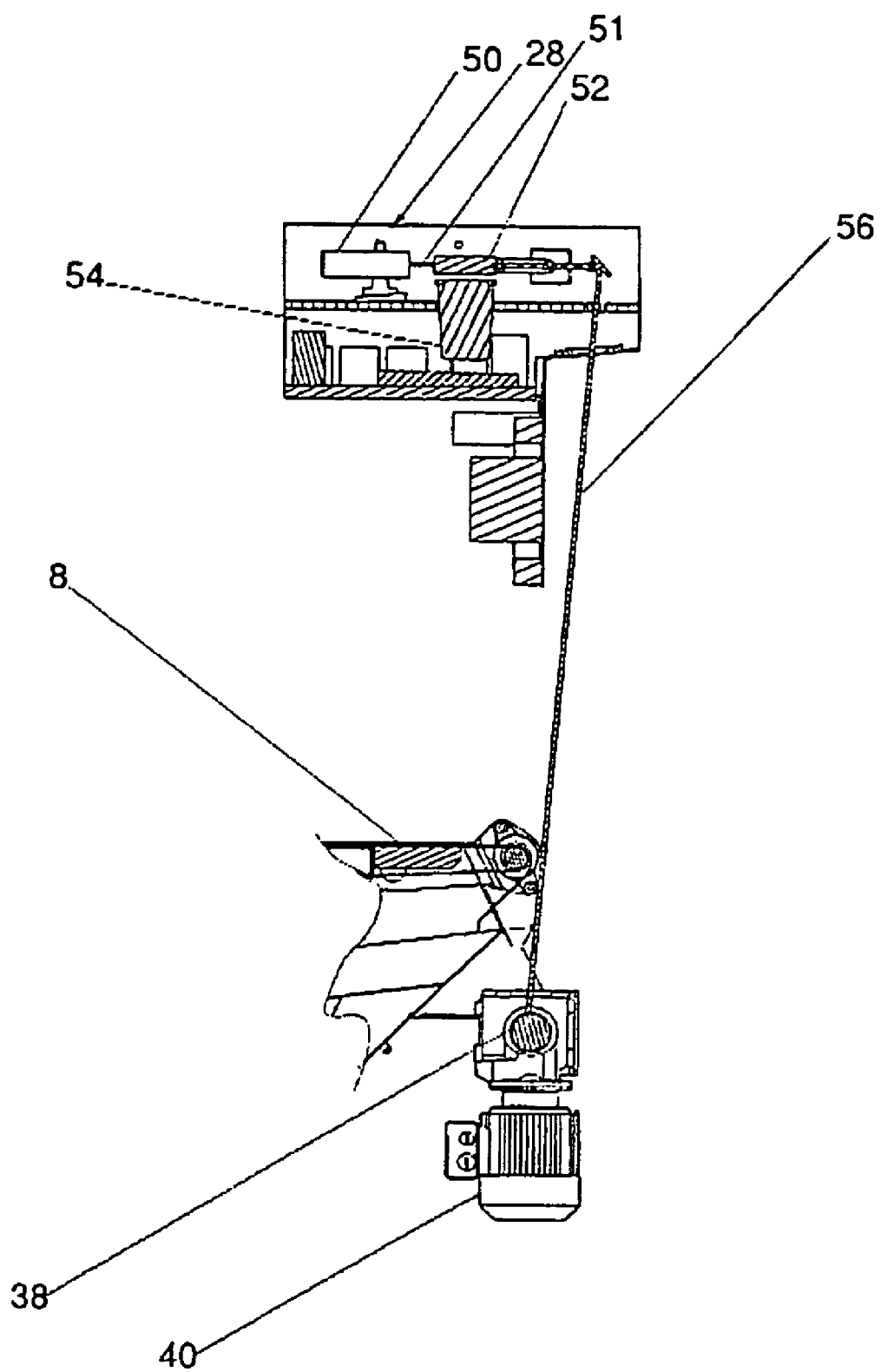
FIG. 2 is a cross sectional view of the upper interrogation station in relation to the feed belt and rotating background.

Now referring to FIG. 2, a cross-section view of the upper interrogation station 28 is shown in relation to the interrogation background 38 and the feed conveyor 8. The upper interrogation station 28 includes a laser 50 that provides an electromagnetic emission 51 that is directed to a rotating mirror 52 which is turned by a scanning Motor 54. The electromagnetic emission 51 is reflected from the scanning mirror 52 to form a scanning line 56 which is used to both illuminate the articles in the product stream 2 (FIG. 1) and to capture the reflected portion of the electromagnetic emissions 51 that is reflected from the articles in the product stream 2 as they pass through the upper interrogation zone 30. It should be understood that the lower interrogation station 32 is similarly constructed and includes similar elements.

Figure 3:
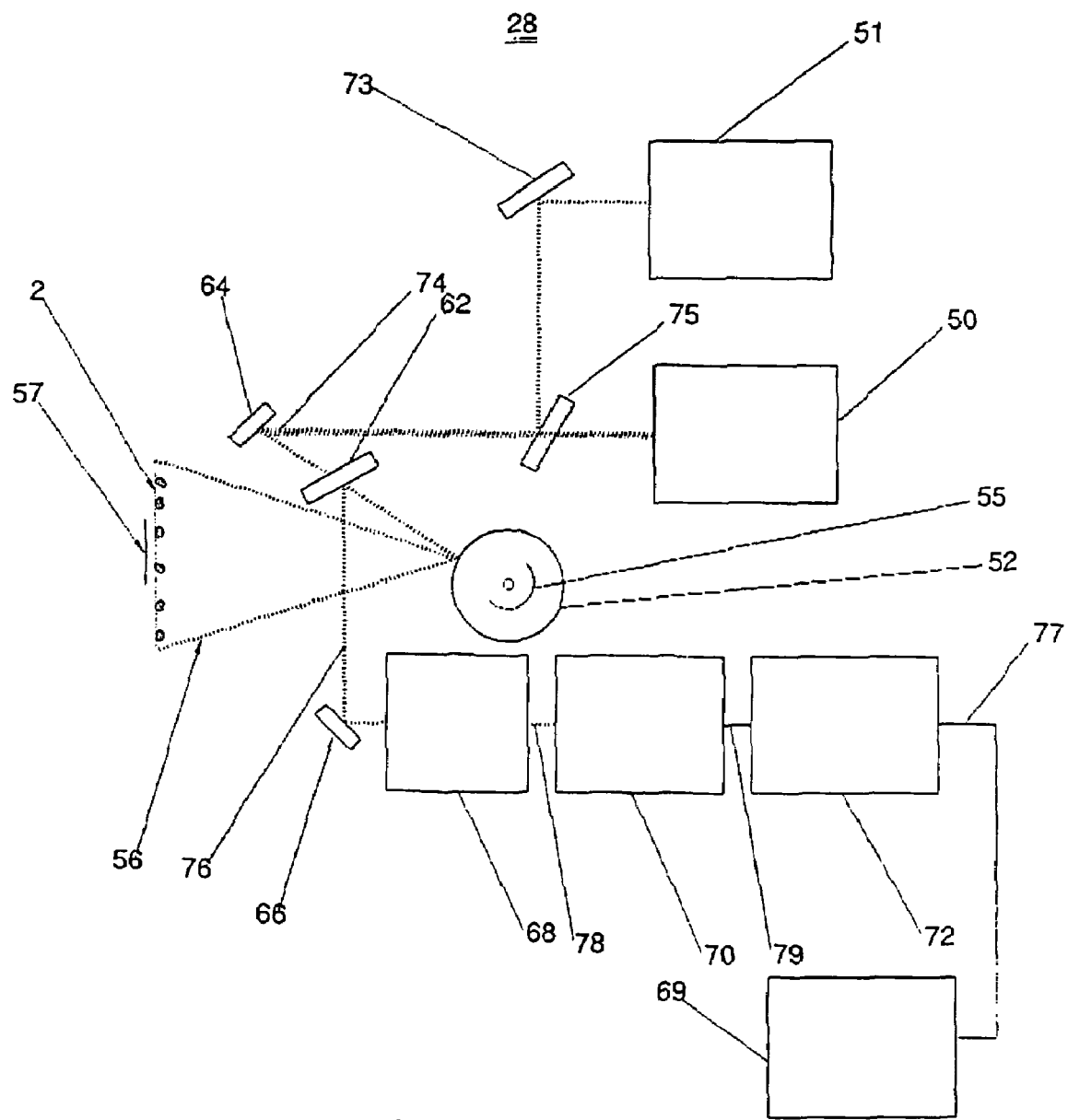
FIG. 3 is a block diagram of the interrogation station.

Now referring to FIG. 3, a block diagram of an upper and lower interrogation station (28 and 32 respectively) is shown. Here, an electromagnetic emission 74 is generated by a an electromagnetic source 50 having a first wavelength. In a preferred embodiment, the electromagnetic source 50 is a laser. The electromagnetic emission 74 is directed towards a folding mirror 64 through a separation mirror 62. The separation mirror 62 is configured to pass the electromagnetic emission 74 without altering the polarization of the emission. After passing through the separation mirror 62, the electromagnetic emission is directed towards a rotating mirror 52 that is turned in a motor rotation direction 55 at a fixed angular velocity. In a preferred embodiment, the rotating mirror 52 is a multifaceted mirror having a number of sides and preferably twelve total sides. Yet further, it should be understood that the rotating mirror 52 may alternatively be a galvanic scanner (not shown). The geometry of the scanning mirror 52 is specified to provide a scanning line over a specified distance at a specific rate that is partially determined by the speed of the motor (not shown) and number and size of the mirror facets.

The scanning line 56 (FIG. 2 and FIG. 3) is configured to scan the electromagnetic emission across the product stream 2 in the direction generally indicated by the arrow 57. The articles in the product stream 2 reflect a portion of the electromagnetic emission 74 of the scanning line 56 or from the background (FIG. 2). The portion of the reflected electromagnetic emission from the product stream is generally indicated by the numeral 76 and travels to the scanning mirror 52 where it is reflected to the separation mirror 62. This mirror reflects a portion reflected radiation from the articles in the product stream 76 to the folding mirror 66. The reflected electromagnetic energy is then directed toward a collector lens 68 where the electromagnetic energy is focused as generally indicated by numeral 78.

The focused portion of the reflection of the electromagnetic energy from the product stream 78 is directed to an optical processing and conversion module 70. This module provides optical processing to divide the electromagnetic energy into various streams of unique polarization parameters and then converts these streams into individual electrical signals, becoming optical sensor electrical signals 79 which are delivered to the control circuitry formed here by a classifying processor 72. A preferred embodiment of the module 70 in combination with processor 72 is shown in detail in FIG. 4.

The classifying processor 72 receives the optical sensor electrical signals 79 and provides mathematical transforms and algorithms to derive numerical parametric data based that are associated with each article. The numerical parametric data is compared against user information in the form of sorting criteria to determine whether an article is desirable article 4 or undesirable 6. The classifying processor 72 delivers an ejector signal 77 to ejector assembly 69 that is synchronized to the product stream 2 to remove undesirable articles 4.

Figure 4:
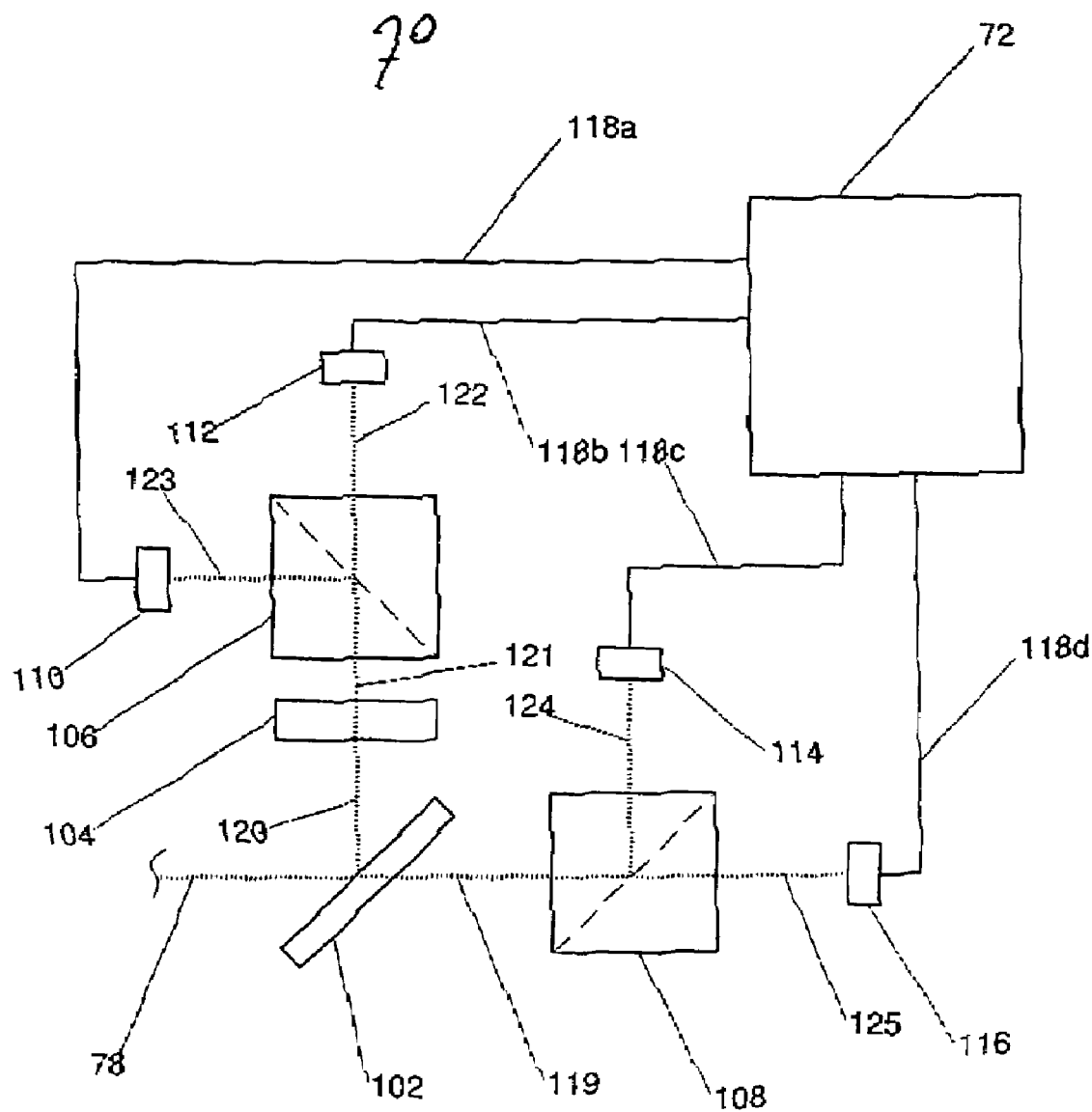
FIG. 4 is a block diagram of a four polarization state optical processing and conversion unit.

Now referring to FIG. 4, a configuration of the optical processing and conversion assembly 70 for a single wavelength is shown in block diagram detail. Here, four polarization characteristics are identified and measured as discussed below. The portion of the reflected electromagnetic emission from the product stream that is focused is generally indicated by the numeral 78 and is directed to a 50/50 beam splitter 102 where approximately one half of the radiation 78 is reflected as radiation 120 and approximately one half is passed as radiation 119. The portion of the electromagnetic radiation that passes through the 50/50 beam splitter 102 as indicated by numeral 119 encounters a first polarizing been splitter 108 configured to pass horizontally polarized electromagnetic radiation generally indicated by numeral 125 and reflect the non-horizontally polarized electromagnetic radiation generally indicated by the numeral 124. The horizontally polarized portion of the electromagnet radiation 125 is directed to a first optical sensor 116 which converts the electromagnetic radiation 125 into an electrical signal 118 D that is routed to the classifying processor 72. That portion of the electromagnetic radiation 119 that is reflected by the first polarizing been splitter 108 as generally by numerical 124 is directed to a second optical sensor 114 configured to convert the electromagnetic radiation into an electrical signals as indicated by numerical 118 C that is further routed to the classifying processor 72.

That portion of the reflected electromagnetic radiation from the product stream 78 that is reflected by the 50/50 beam splitter 102 is generally indicated by the numeral 120. This radiation is directed a retarder 104 which is configured to delay the electromagnetic radiation 120 by one quarter wavelength, and becomes the electromagnetic radiation indicated as generally indicated as 121. The electromagnetic radiation 121 is directed to the second polarizing been splitter 106 which is configured to similarly pass or is horizontally polarized electromagnetic radiation and reflect the non-horizontally or vertically polarized radiation. As is well known in the art, the electromagnetic radiation 121, after having been modified by the retarder 104, is useful for detecting the presence or absence of circularly polarized light. That portion of the electromagnetic radiation that passes through the polarizing been splitter 106 as generally indicated by the numeral 122 is captured by a third optical sensor 112 that converts the electromagnetic energy into electrical signals 118*b* and is routed to the classification processor 72. The portions of the electromagnetic radiation that are reflected by the second polarizing been splitter 106 is generally indicated by the numeral 123 and is directed to a fourth optical sensor 110 that converts the electromagnetic radiation into an electrical signal 118*a* that is routed to the classified processor 72.

In a preferred embodiment, the optical sensors 110, 112, 114 and 116 are photo-multiplier tubes.

The classified processor 72 is capable of combining the first and second electrical signals 118 C and 118 D representing radiant power of two perpendicular polarized states into a degree for depolarization according to equation (2). The degree of depolarization can be compared with a threshold value from a memory (not shown) connected to the processor 72 in order to decide on acceptance of the object corresponding to the measured degree of depolarization. The degree of depolarization offers specifically extra contrast for products having low reflectance.

Additionally the signals 118 A and 118 B can be used in the algorithm used in the decision means 72 according to the invention. A algorithm could use the concurrent combination of the signals 118 A, 118 B and the calculated degree of depolarization.

During an initialization the processor 72 can be programmed. In a preferred embodiment a translucent cylinder is used for initialization. During initialization the cylinder is scanned and maximum and minimum values measured during the scan can be used a threshold values.

The electrical signals are generated at regular intervals. A combination of the first and second electrical signals corresponds to the polarized state of a pixel in the scanning zone. The subsequent pixels can be stored and combined to form an image of the scanning zone, showing the objects that have passed through the scanning zone.

In an embodiment the algorithm takes into account multiple pixels, e.g. an area of pixels.

Figure 5:
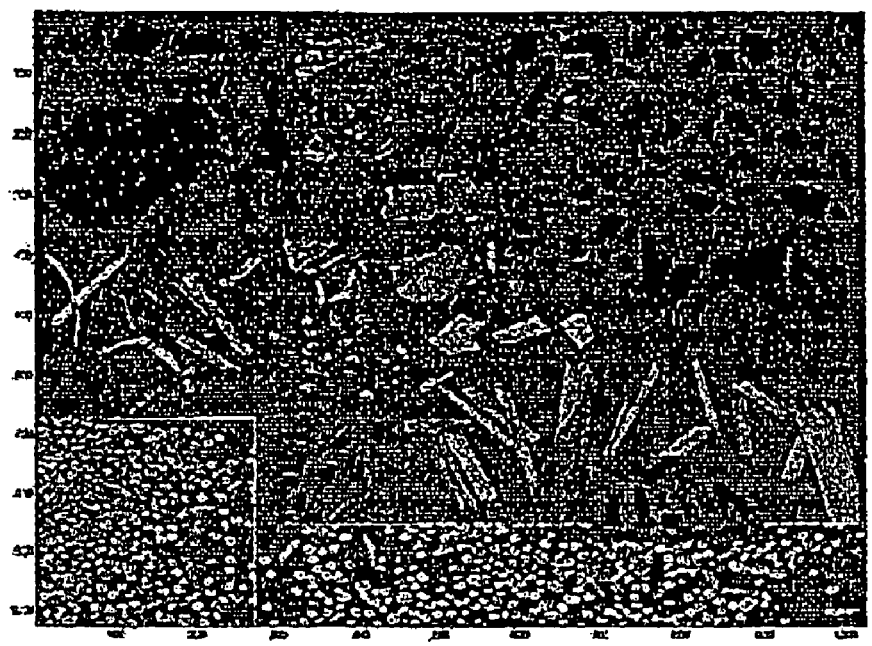
FIG. 5 shows two scanned images for reflectance and degree of depolarization made with an apparatus according to invention of a mix of frozen vegetable.
Figure 5:
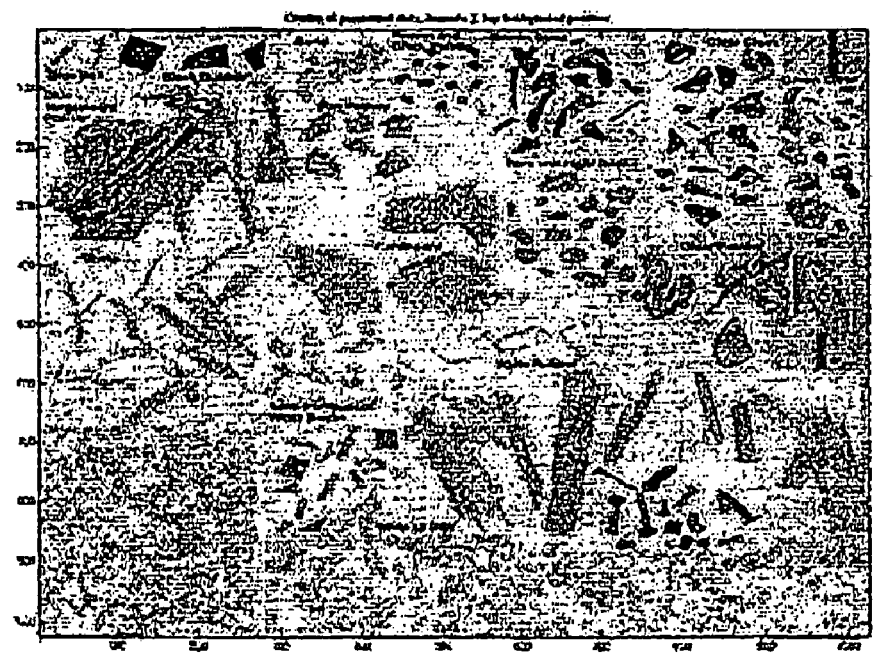

FIG. 5 shows two pictures build of pixels of scanned articles in a product stream on an apparatus according to the invention. Every pixel represents a scanned point of the articles.

The top picture shows the radiant power of reflected radiation from the scanned articles. Every pixel represents the radiant power of scattered reflected light. The top picture represents a collection of pixels. The values for the third electrical signal from the third detection means according to the invention have been captured. The picture is the result of collecting electrical signals over a predetermined time.

The picture shows light and dark articles. The articles represent a mix of frozen products.

The bottom picture of FIG. 5 shows the degree of depolarization according to equation (2) which is a combination of two electrical signals detected by two detection means. The laser light beam from the emitter section has a first state of polarization. The first detector, in conjunction with a polarization beam splitter such a wire grid, is adapted to measure the radiant power of the reflected radiation having the same polarization state. A second detector is adapted to measure the perpendicular polarization. The two corresponding signals are combined according to equation (2) in the decision section in order to obtain a value for the depolarization.

The bottom picture of FIG. 5 represents several consecutive combinations of electrical signals, each forming a pixel of the image. The bottom picture shows the same products as the top picture.

It is clear the dark object, e.g. the object near the upper left corner has more contrast in the image constructed from the values for depolarization. Therefore the combination of electrical signals representing different states of polarization improve contrast and thus improve the classification of articles.

Figure 6:
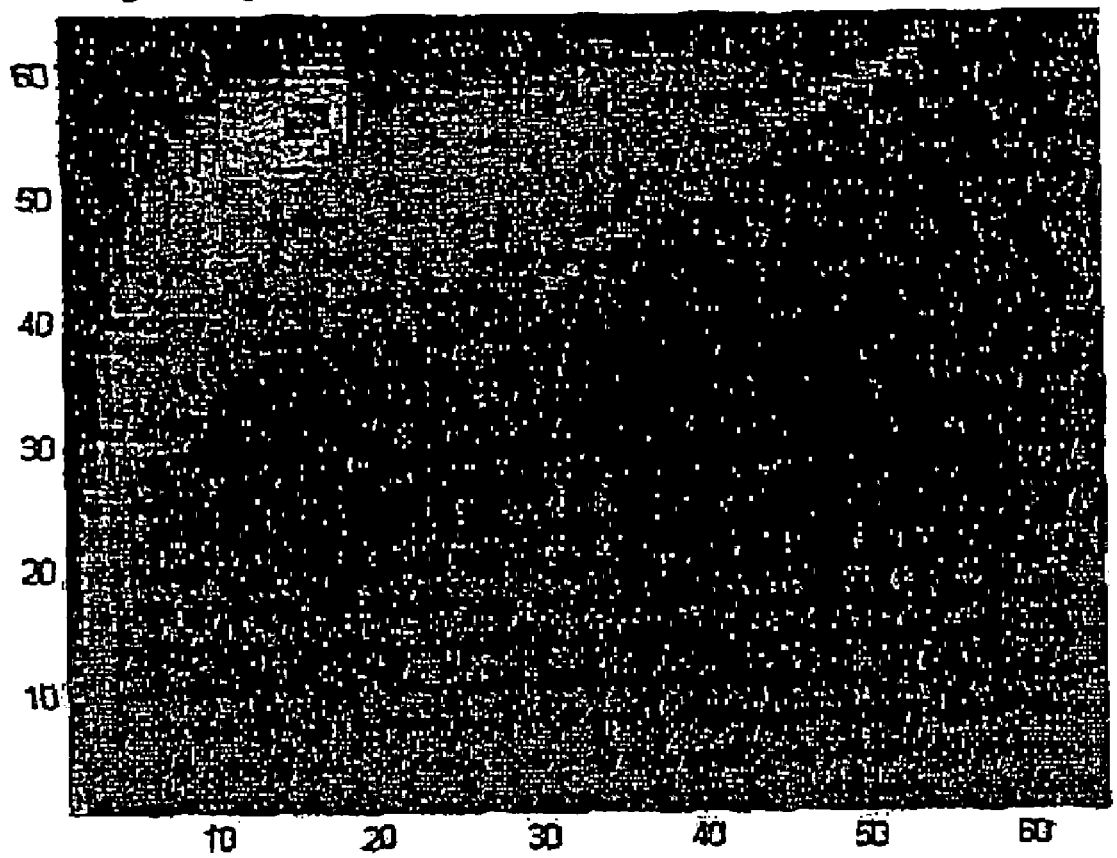
FIG. 6. shows a histogram of processed pixel data of the images of FIG. 5.

FIG. 6 illustrates a combined 2D-histogram of the two images from FIG. 5. On a horizontal axis the radiant power is depicted, on the vertical axis the degree of depolarization is indicated. A relationship between radiant power and degree of depolarization is indicated. For low reflectance, left hand side of the histogram, contrast of scanned articles is more pronounced in values for degree of depolarization.

As indicated in the lower left hand side of the histogram, a large number of pixels has a low degree of polarization and a low reflectance. These values can be filtered out and could be left out of the algorithm for classification.

In an embodiment the third detection means can be adapted to detect translucency. In another embodiment a fourth detection means can be added to detect and convert translucency into an electrical signal to be processed by the control circuitry.

Figure 7:
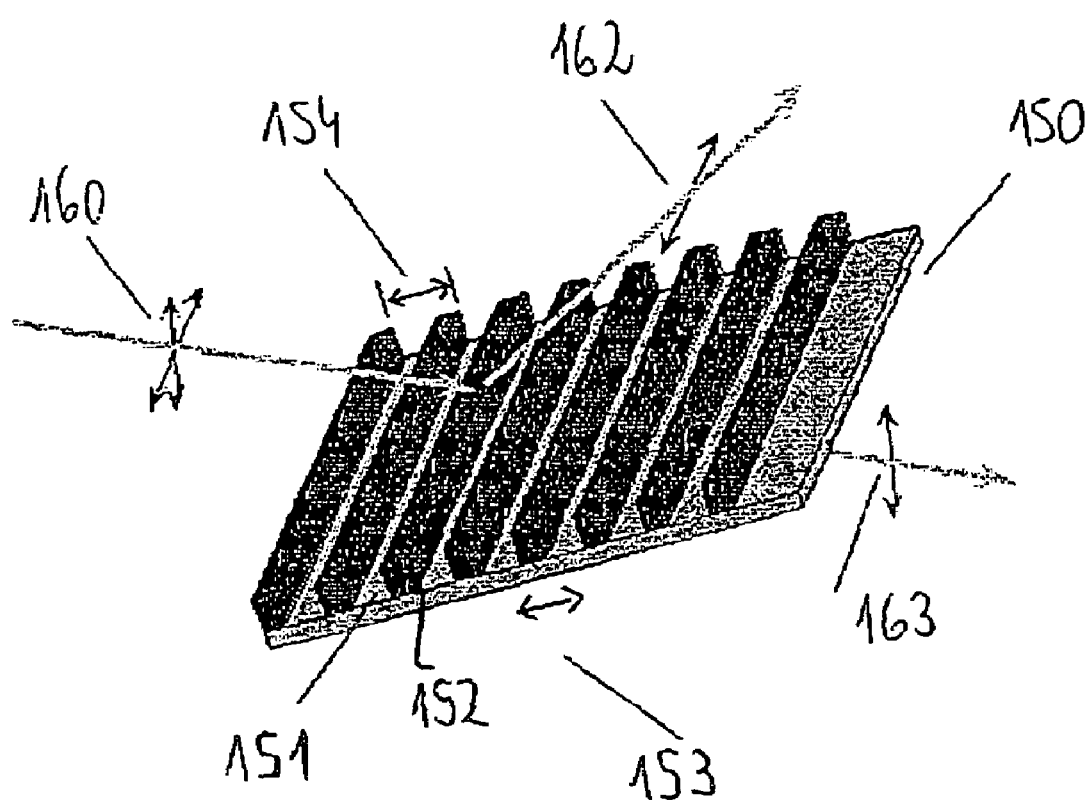
FIG. 7 shows a perspective view of polarizing wire grid according to preferred embodiment.

FIG. 7 shows a polarized beam splitter 150 according to a preferred embodiment. On a glass substrate 151 aluminum ribs 152 forming microwires are deposited. The wires are deposited parallel and have a line width indicated by arrow 153. The wires 152 are deposited at a constant period indicated by arrow 154.

In FIG. 7 it is illustrated that a beam of unpolarized light 160 is directed toward the beam splitter 150. The S-plane polarized light 162 is reflected by the surface of microwire 152, while P-plane polarized light 163 is transmitted.

The polarized beam splitter 150 according to FIG. 7 is advantageous in the scanning apparatus according to the invention.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. An apparatus for classifying articles comprising,
transport means connected to a frame for directing articles having a transport direction, such that a product stream is created,
at least an emitter section connected to the frame, the emitter section comprising at least one radiation source of electromagnetic radiation having at least a first wavelength and an initial polarization ($P_0$), wherein radiation from the radiation source is directed towards a scanning zone, wherein the articles move through the scanning zone,
at least a detection section connected to the frame for detecting at least a portion of radiation reflected by articles in the scanning zone, the detection section comprising at least a first detection means for converting radiant power of the portion of reflected radiation having a first polarization state ($P_1$) into a first electrical signal ($E_1$), at least a second detection means for converting radiant power of the portion of reflected radiation having a second different polarization state ($P_2$) into a second electrical signal ($E_2$), and a third detection means for converting radiant power of the portion of reflected radiation into a third electrical signal (I),
control circuitry in operable communication with the detection section for receiving the electrical signals, wherein the control circuitry comprises decision means for generating a selection signal ($S_1$) based on the received electrical signals and threshold values from a memory, and
selection means for separating products from the product stream arranged downstream from the detection section, wherein the selection means are actuated to separate an article from the product stream according to the received selection signal ($S_1$) from the control circuitry.

2. The apparatus for classifying articles as claimed in claim 1, wherein the control circuitry is adapted to combine the first and second electrical signals ($E_1$ and $E_2$) to form a signal corresponding to the polarization state of the portion of reflected radiation.

3. The apparatus for classifying articles as claimed in claim 2, wherein the first and second electrical signals ($E_1$ and $E_2$) are combined to correspond to a degree of depolarization.

4. The apparatus for classifying articles as claimed in claim 2, wherein a plurality of user defined coefficients designated as $C_{01}, C_{02}, C_{11}, C_{12}$ are stored in the memory, and the control circuitry further comprises an arithmetic unit which is configured to perform a mathematical transformation to provide a first polarization parameter $P_0$ which is a function of a first combination of the first and second signal data values $E_1$ and $E_2$ and the user defined coefficients $C_{01}, C_{02}, C_{11}$, and $C_{12}$ and yet further provides a second polarization parameter $P_1$, which is a function of a second combination of the first and second electrical signal values ($E_1$ and $E_2$) and the user defined coefficients $C_{01}, C_{02}, C_{11}$, and $C_{12}$.

5. The apparatus for classifying articles as claimed in claim 4, wherein the arithmetic unit is configured to perform the mathematical transformation to provide the first polarization value $P_0$ so that $P_0=E_1\times C_{01}+E_2\times C_{02}$, and is further configured to provide the second polarization value $P_1$ so that $P_1=(E_1\times C_{11}+E_2\times C_{12})/P_0$.

6. The apparatus for classifying articles as claimed in claim 4, wherein the first polarization state is horizontal and the second polarization state is vertical, and wherein the arithmetic unit is configured to perform the mathematical transformation to provide the first polarization value $P_0$ so that $P_0=E_1\times C_{01}+E_2\times C_{02}$, and is further configured to provide the second polarization value $P_1$ so that $P_1=E_1\times C_{11}+E_2\times C_{12}$.

7. The apparatus for classifying articles as claimed in claim 1, wherein the decision means are adapted to utilize the first and second electrical signals ($E_1$ and $E_2$) as decision criteria for low light reflectance of the reflected radiation.

8. The apparatus for classifying articles as claimed in claim 7, wherein the low light reflectance is defined by 0-20% of the maximum radiant power of reflected radiation.

9. The apparatus for classifying articles as claimed in claim 8, wherein the decision means are adapted to primarily make a termination of acceptance using a comparison of the degree of depolarization and a threshold from memory for objects having a low reflectance.

10. The apparatus for classifying articles as claimed in claim 1, wherein the control circuitry provide the electrical signals ($E_1$ and $E_2$) at a regular time intervals.

11. The apparatus for classifying articles as claimed in claim 10, wherein the control circuitry provides a filter for filtering concurrent electrical signals representing low reflectance and a low degree of depolarization.

12. The apparatus for classifying articles as claimed in claim 1, wherein the detection section comprises at least a beam splitter for splitting the reflected radiation, directing the reflected radiation to first & second detection means and the third detection means.

13. The apparatus for classifying articles as claimed in claim 1, wherein the receiving section comprises at least one polarizing beam splitter for splitting the portion of reflected radiation between a first polarization state and a second polarization state.

14. The apparatus for classifying articles as claimed in claim 13, wherein the first detection means is positioned to receive radiation reflected by the polarizing beam splitter, and wherein the second detection means is positioned to receive radiation passing through the polarizing beam splitter.

15. The apparatus for classifying articles as claimed in claim 13, wherein the polarizing beam splitter is a wire grid polarization element.

16. The apparatus for classifying articles as claimed in claim 15, wherein the wire grid polarization element comprises a layer of generally parallel metal wires on a glass substrate.

17. The apparatus for classifying articles as claimed in claim 16, wherein the metal wires comprise aluminum wires.

18. The apparatus for classifying articles as claimed in claim 1, wherein the radiation source is adapted to emit a coherent beam of radiation having a given cross sectional area.

19. The apparatus for classifying articles as claimed in claim 18, wherein the first, second and third detection means have a field of view generally of the order of magnitude of the cross sectional area.

20. The apparatus for classifying articles as claimed in claim 18, wherein the emitter section comprises a scanning mirror, and wherein the electromagnetic radiation is reflected by the scanning mirror toward the product stream, and is further swept in a transverse direction relative to the conveying direction.

21. The apparatus for classifying articles as claimed in claim 20, wherein the scanning mirror comprises a high speed rotating polygon mirror.

22. The apparatus for classifying articles as claimed in claim 20, wherein the scanning mirror is configured to reflect a portion of the electromagnetic radiation that is reflected from the articles in the product stream as an electromagnetic signal that is transmitted to the detection section.

23. The apparatus for classifying articles as claimed in claim 20, wherein the apparatus has an initialization state and the memory is adapted for storing at least two selection values ($V_1$, $V_2$) for at least two polarization states of reflected light having an initial polarization from an article detected during the initialization state.

24. The apparatus for classifying articles as claimed in claim 1, wherein the apparatus is further configured to remove undesirable articles from the product stream, and wherein the control circuitry is further configured to provide a label for each article based on a first comparison of a set of electrical signals associated with each article to a first decision criteria and on a second comparison of a set of electrical signals associated with each article to an second decision criteria, and wherein the label indicates the state of the article as a desirable article or an undesirable article, and wherein the control circuitry is further configured to provide an ejection signal as selection signal for each article that has the label of an undesirable article.

25. The apparatus for classifying articles as claimed in claim 1, further comprising a plurality of detection sections each directed toward the product stream wherein one or more detection section is positioned above the product stream and one or more detection section is positioned below the product stream.

26. A method for classifying products, comprising:
providing a product stream, scanning the products by emitting electromagnetic radiation toward the product stream having an initial polarization and generating at least two electrical signals corresponding to radiant power of different polarization directions, said radiant power coming from the reflected radiation from the scanned product and a third electrical signal corresponding to the radiant power of the reflected light, making a determination on classification of the article in the product stream based on the generated electrical signals and selection values provided by a user and redirecting the product from the stream based on the decision results.

27. The method as claimed in claim 26, wherein the first and second electrical signals are combined to form a signal corresponding to the polarization state of the reflected radiation.

28. The method as claimed in claim 26, wherein the first and second electrical signals are combined to correspond to a degree of depolarization.

29. The method as claimed in claim 26, wherein the first and second electrical signals provide the basis for making a determination for objects having a low light reflectance.

30. The method as claimed in claim 29, wherein the low light reflectance is defined by 0-20% of the maximum radiant power of reflected radiation.

31. The method as claimed in claim 30, wherein the basis for making a determination comprises comparing a degree of depolarization and a threshold from memory for objects having a low reflectance.

32. The method as claimed in claim 26, wherein the electrical signals are provided at regular time intervals.

33. The method as claimed in claim 32, wherein concurrent electrical signals representing low reflectance and a low degree of depolarization are filtered before making a decision.

34. The method as claimed in claim 26, wherein the reflected radiation is split in a beam splitter, directing the reflected radiation to first and second detection means and the third detection means.

35. The method as claimed in claim 34, wherein the reflected radiation is routed to a polarizing beam splitter splitting the reflected radiation in a portion having a first polarization state and a second polarization state.

36. The method as claimed in claim 35, wherein the polarizing beam splitter is a wire grid polarization element.

37. The method as claimed in claim 26, wherein the emitted electromagnetic radiation comprises a coherent beam of electromagnetic radiation having a given cross sectional area is emitted.

38. The method as claimed in claim 37, wherein the reflected radiation is detected over an area corresponding generally with the order of magnitude of the given cross sectional area.

39. The method as claimed in claim 37, wherein the coherent beam of electromagnetic radiation is reflected by a scanning mirror toward the product stream and is further swept in a transverse direction relative to the conveying direction.

40. The method as claimed in claim 39, wherein the scanning mirror comprises a high speed rotating polygon mirror.

41. The method as claimed in claim 37, wherein a portion of the electromagnetic radiation is reflected by the products and is transmitted to the detection section by the scanning mirror.

42. The method as claimed in claim 37, wherein the method further comprises the step of initializing by storing at least two values ($V_1$, $V_2$) for at least two polarization states of reflected light having an initial polarization from a product detected during the initialization.

* * * * *